United States Patent
Ishii

(10) Patent No.: US 8,900,205 B2
(45) Date of Patent: Dec. 2, 2014

(54) SYRINGE FOR PREFILLED SYRINGE

(71) Applicant: Terumo Kabushiki Kaisha, Shibuya-ku (JP)

(72) Inventor: Naoki Ishii, Ashigarakami-gun (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 0 days.

(21) Appl. No.: 13/755,337

(22) Filed: Jan. 31, 2013

(65) Prior Publication Data

US 2013/0197451 A1    Aug. 1, 2013

Related U.S. Application Data

(60) Provisional application No. 61/592,775, filed on Jan. 31, 2012.

(51) Int. Cl.
| | |
|---|---|
| A61M 5/315 | (2006.01) |
| A61M 5/31 | (2006.01) |
| C08F 28/02 | (2006.01) |
| C08F 20/68 | (2006.01) |
| C08F 18/22 | (2006.01) |
| C09D 5/16 | (2006.01) |

(52) U.S. Cl.
CPC ........... *A61M 5/31513* (2013.01); *C08F 28/02* (2013.01); *A61M 5/3129* (2013.01); *C08F 20/68* (2013.01); *A61M 5/3148* (2013.01); *A61M 5/3146* (2013.01); *C08F 18/22* (2013.01); *C09D 5/1637* (2013.01)
USPC .......................................... 604/230; 604/218

(58) Field of Classification Search
CPC .......... A61M 5/31513; A61M 5/3148; A61M 5/3146; A61M 5/3129; C08F 18/22; C08F 28/02; C08F 20/68; C09D 5/1637

USPC ................................................ 604/218, 230
See application file for complete search history.

(56) References Cited

U.S. PATENT DOCUMENTS

| | | | |
|---|---|---|---|
| 6,040,415 A | 3/2000 | Arimori et al. | |
| 6,461,334 B1 * | 10/2002 | Buch-Rasmussen et al. | 604/230 |

(Continued)

FOREIGN PATENT DOCUMENTS

| | | |
|---|---|---|
| JP | 2001-508480 A | 6/2001 |
| JP | 2004-008509 A | 1/2004 |

(Continued)

OTHER PUBLICATIONS

International Search Report (Forms PCT/ISA/220 and PCT/ISA/210) and the Written Opinion of the International Searching Authority (Form PCT/ISA/237) issued on May 7, 2013, in corresponding International Application No. PCT/JP2013/052250. (9 pages).

(Continued)

*Primary Examiner* — Ling Choi
*Assistant Examiner* — David L Miller
(74) *Attorney, Agent, or Firm* — Buchanan Ingersoll & Rooney PC

(57) ABSTRACT

An object of the present invention is to provide a syringe for prefilled syringe in which the adsorption of a low-molecular medical agent or a protein for a long term is precluded. In accordance with the present invention, the above-described object is achieved by a syringe for prefilled syringe including: a plunger in which a gasket is attached to a top; and a syringe barrel in which the plunger is slidably accommodated, wherein the surface of the gasket and the inner wall of the syringe barrel are subjected to surface modification with a polymer containing zwitterion.

5 Claims, 7 Drawing Sheets

(56) References Cited

U.S. PATENT DOCUMENTS

| | | |
|---|---|---|
| 6,673,883 B1 | 1/2004 | Rowan |
| 2008/0181861 A1* | 7/2008 | Jiang et al. ............... 424/78.09 |

FOREIGN PATENT DOCUMENTS

| | | |
|---|---|---|
| JP | 2005-027831 A | 2/2005 |
| JP | 2006-167110 A | 6/2006 |
| JP | 2009-508542 A | 3/2009 |
| JP | 2009-108310 A | 5/2009 |
| JP | 2009-153586 A | 7/2009 |
| JP | 2013-006996 A | 1/2013 |
| WO | 98/46659 A1 | 10/1998 |
| WO | 2012/165525 A1 | 12/2012 |

OTHER PUBLICATIONS

Zhang et al., "Superlow Fouling Sulfobetaine and Carboxybetaine Polymers on Glass Slides" Langmuir, (Oct. 2006), vol. 22, No. 24, pp. 10072-10077.

* cited by examiner (a)(b)(c)

(a)(b)(c)

SYRINGE FOR PREFILLED SYRINGE

BACKGROUND OF THE INVENTION

1. Technical Field

The present invention relates to syringes for prefilled syringe.

2. Description of the Related Art

A prefilled syringe refers to a syringe filled with a medical agent. The syringe for prefilled syringe is comprised of: a syringe barrel which includes a nozzle in its top and an opening mouth in its proximal end; and a plunger which is a pushing tool that can slide liquid tightly on the inner surface of the syringe barrel. The syringe for prefilled syringe has the structure in which the top of the nozzle is sealed with a sealant, the sealant is opened during its use, and the plunger is pushed to dispense the medical agent. Further, in order to make the inner surface of the syringe barrel liquid-tight and slidable, the diameter of a gasket attached to the top of the plunger is designed to be greater than the inner diameter of the syringe barrel and a lubricant such as a silicone oil is applied to the inner surface of the syringe barrel and the surface of the gasket.

In general, it is necessary to suck a drug solution into a syringe when an injection drug in an ampoule or a vial is administered to a patient. According to the Pharmaceutical Society of Japan, however, "promotion of efficiency of work in a clinical situation", "prevention of a medical accident such as the mix-up or incorrect administration of a drug solution", and "reduction in the risk of contamination with a foreign substance or bacterial contamination" can be expected by omitting this manipulation in the case of a prefilled syringe, while, for commercializing prefilled syringes, it becomes important to examine the stability of drug solutions, preservative quality by plastic containers, and the like.

Especially, there is a problem that the stability of a drug solution is deteriorated by dissolving and diffusing a lubricant used for allowing a plunger to be liquid-tight and slidable on the inner surface of a syringe barrel, in the drug solution filled in the syringe. That is, for example, when a silicone oil is used as the lubricant, the silicone oil dissolved in the drug solution in the syringe might be adsorbed in a low molecular medical agent to adversely affect the long term stability of a preparation.

Technologies for solving such problems include that in Japanese Patent No. 2005-27831-A. In Japanese Patent publication No. 2005-27831-A as described above, there is disclosed a prefilled syringe including: a syringe body including a nozzle in one end side; a plunger inserted into the syringe body from another end side; and a liquid reservoir for reserving a liquid in the syringe body and discharging the liquid from a nozzle side as described above by reducing an internal volume by a pressing force from the plunger, the prefilled syringe including a structure in which a first engagement portion is formed on the inside of the syringe body and a second engagement portion engaged with the first engagement portion in a direction of moving the plunger in the syringe body is formed in the plunger. In accordance with the prefilled syringe of Japanese Patent publication No. 2005-27831-A, contamination of foreign substances into a medical agent can be avoided since a drug solution is sealed in a drug solution reservoir (bag 50) which is formed a bag-shaped film sheet body.

Further, other technologies for avoiding contamination of foreign substances into a medical agent include that in Japanese Patent publication No. 2006-167110-A. In Japanese Patent publication No. 2006-167110-A as described above, there is disclosed a syringe in which a dispersion containing a fluorinated resin, a silicone resin, a urethane resin and fine particles is applied to an inner surface of the syringe barrel and a gasket surface to form a coating layer. In accordance with the syringe of Japanese Patent publication No. 2006-167110-A, the syringe allows the avoidance of contamination of foreign substances into an medical agent and stably has high slidability since the fluorinated-resin and the silicon resin act as components for imparting slidability and the urethane resin acts as a component for imparting flexibility.

SUMMARY OF THE INVENTION

In the prefilled syringe of Japanese Patent publication No. 2005-27831-A as described above, the problem that the lubricant applied to the inner surface of the syringe barrel and the surface of the gasket is dissolved in the drug solution is certainly solved since the drug solution is sealed in the bag 50 as illustrated in FIG. 1 and FIG. 7; however, since a problem of the preservative quality of the drug solution by the bag, that is, the relationship between the drug solution and the bag occurs newly, the invention of Japanese Patent publication No. 2005-27831-A does not thoroughly solve the problem that the lubricant is dissolved in the drug solution. Further, for example, since a plurality of ratchet pawls which are engaged with the plunger are regularly placed and formed on the inside of the syringe body in the form illustrated in FIG. 1 of Japanese Patent publication No. 2005-27831-A, the pawls might damage the bag to leak the drug solution from the inside if an operator incorrectly pulls the plunger, so that concerns remain about the stability of the drug solution and the preservability by a plastic container. Furthermore, even if the problem of the damage to the bag is disregarded, since protrusions which are the ratchet pawls are formed on the inside of the syringe body in accordance with the embodiment, it is inferior in slidability to the syringe of Japanese Patent publication No. 2006-167110-A due to the protrusions.

Further, the coating layer containing the composition containing the fluorinated resin, the silicon resin, the urethane resin and the fine particles is formed on the inner surface of the syringe barrel for a syringe and the surface of the gasket in accordance with Japanese Patent publication No. 2006-167110-A as described above, and, therefore, a point contact effect due to a roughened surface structure caused by the fine particles and slidability and flexibility due to the characteristics of each resin can be expected to some extent; however, the slidability is still practically insufficient. Further, since the surface in accordance with Japanese Patent publication No. 2006-167110-A as described above has a roughened surface structure, the surface area of a part directly contacting with the drug solution inevitably becomes large, so that a problem that the agent is easily adsorbed in the roughened surface occurs.

Thus, an object of the present invention is to provide a syringe for prefilled syringe (a prefillable syringe) in which the adsorption of a low-molecular medical agent or a protein for a long term hardly occurs. Another object of the present invention is to provide a syringe for prefilled syringe which has higher slidability than that in the case of coating a silicone oil and can be smoothly manipulated.

In accordance with the present invention, the above-described objects are achieved by a syringe for prefilled syringe comprising of: a plunger in which a gasket is attached to a top; and a syringe barrel in which the plunger is slidably accommodated, wherein the syringe barrel includes an inner wall subjected to surface modification with a polymer containing zwitterion.

The above and other objects, features and advantages of the present invention will become clear from the following description of the preferred embodiments.

DETAILED DESCRIPTION OF THE PREFERRED EMBODIMENTS

A first embodiment of the present invention is a syringe for prefilled syringe comprising of: a plunger in which a gasket is attached to a top; and a syringe barrel in which the plunger is slidably accommodated, wherein the syringe barrel includes an inner wall subjected to surface modification with a polymer containing zwitterion.

As a result, the adsorption of a low-molecular medical agent or a protein for a long term in the syringe can be suppressed and prevented.

In the syringe for prefilled syringe according to the present invention, since a brush-shaped polymer having zwitterion is immobilized on the surface of a site contacting with a drug solution, particularly the inner wall of the syringe barrel, the adsorption of a low-molecular medical agent or a protein for a long term can be suppressed and prevented without dissolution of a lubricant in the syringe.

Further, the surface of the gasket is preferably subjected to surface modification with the polymer containing zwitterion in the syringe for prefilled syringe according to the present invention.

Since the polymer containing zwitterion is thereby immobilized not only on the pressurization surface of the gasket of the syringe for prefilled syringe according to the present invention but also on its side surface, higher slidability is obtained than that in the case of coating a silicone oil.

Therefore, in the syringe for prefilled syringe according to the present invention, the surface of the gasket and the inner wall of the syringe barrel are more preferably subjected to surface modification with the polymer having zwitterion.

As a result, not only the adsorption of a low-molecular medical agent and a protein for a long term in the syringe can be suppressed and prevented, but also higher slidability is obtained than in the case of coating a silicone oil.

Figure 1:
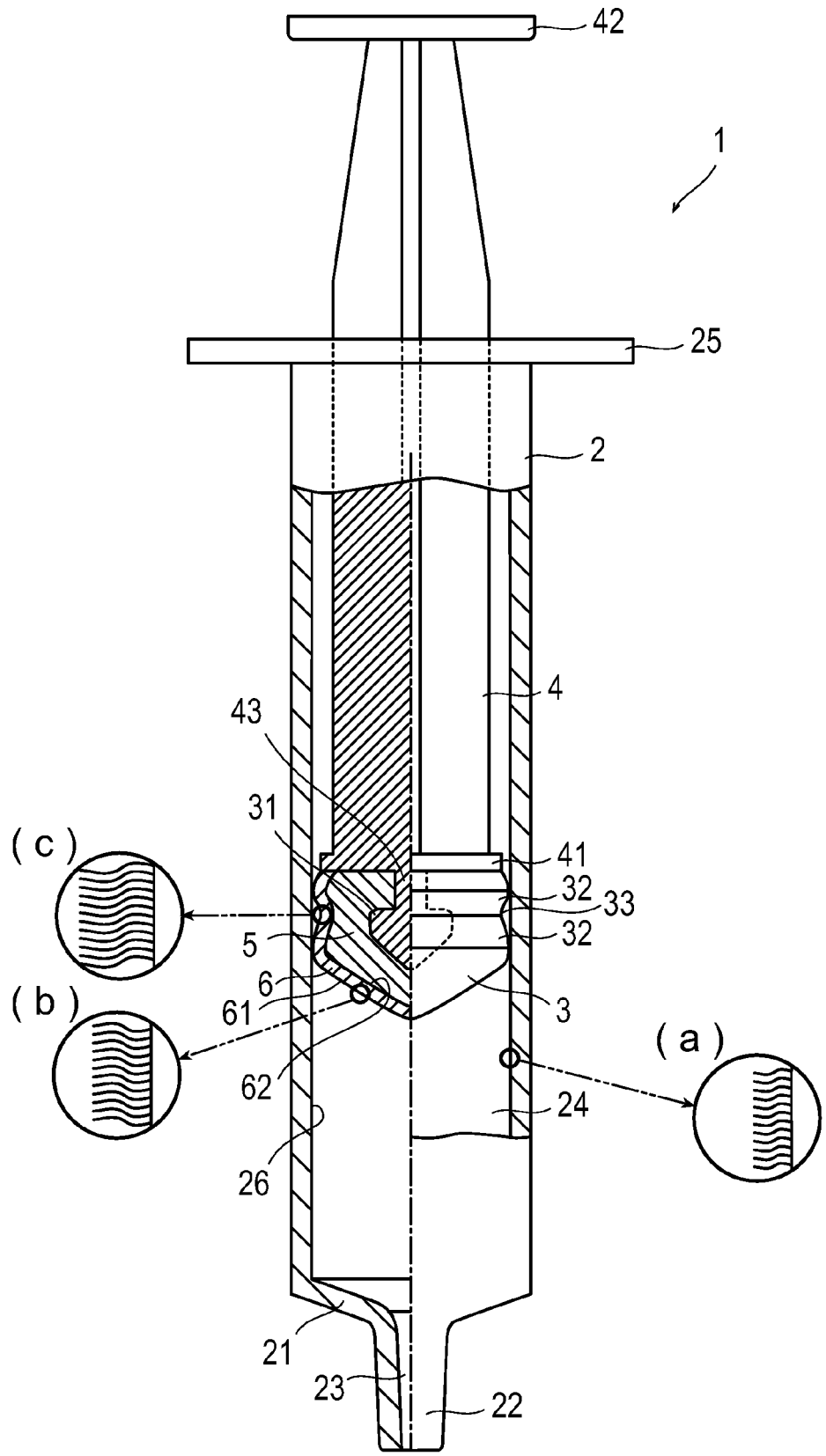
FIG. 1 is a schematic view that illustrates an example of a syringe for prefilled syringe according to the present invention.
Figure 2:
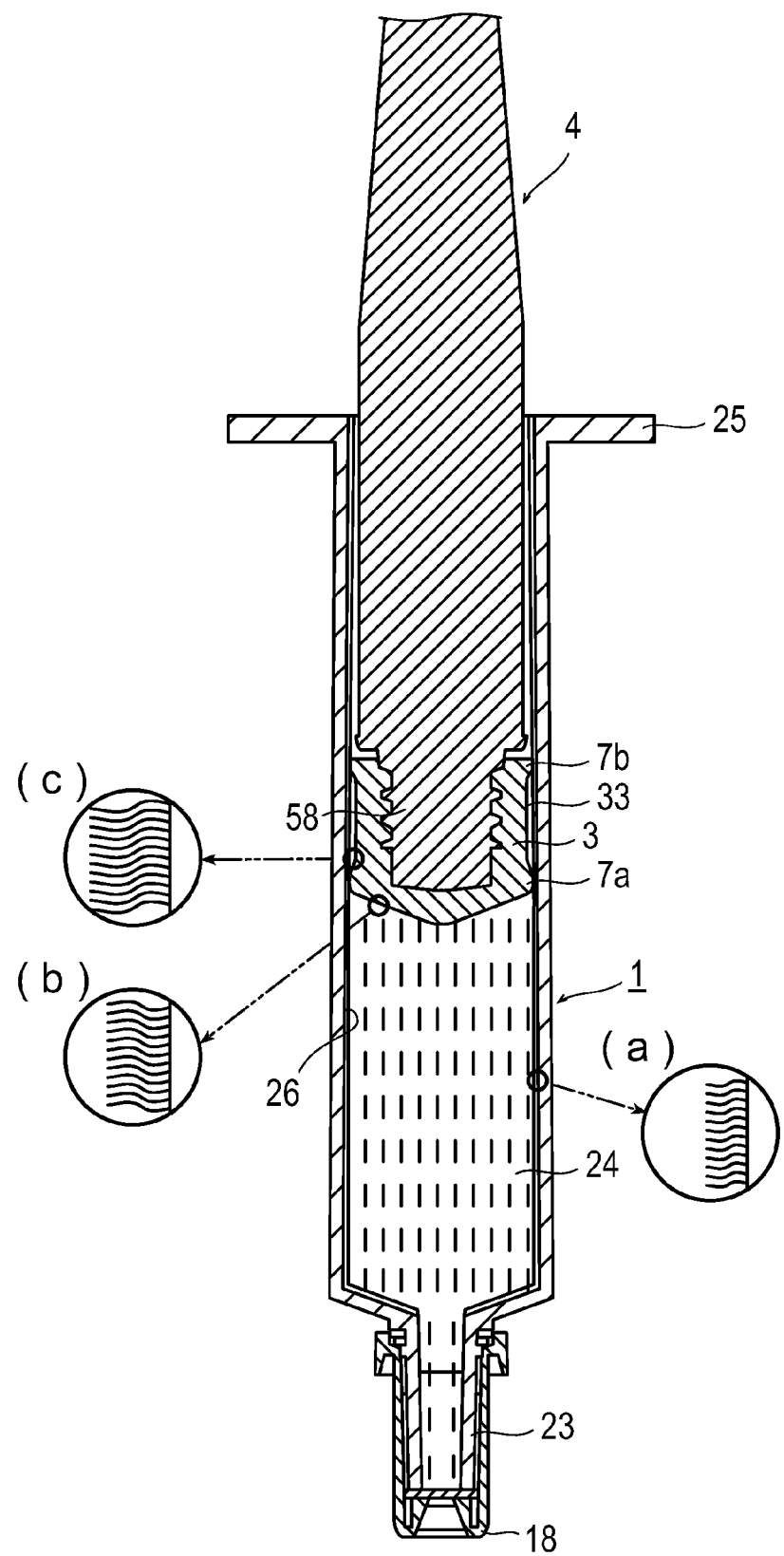
FIG. 2 is a schematic view that illustrates another example of a syringe for prefilled syringe according to the present invention.

In the syringe for prefilled syringe according to the present invention, without particular limitation, a known syringe structure can be applied to the present invention. An example of the constitution of the syringe for prefilled syringe according to the present invention will be explained below with reference to the drawings. As illustrated in FIG. 1, a syringe 1 includes a syringe barrel 2 in which a nozzle 23 which is a needle attaching portion is disposed in its top; a gasket 3 which can slide in the syringe barrel 2; and a plunger 4 which is mounted on the gasket 3 to manipulate the gasket 3 to move. Also, a sealing member 18, with which the nozzle 23 of the syringe barrel is sealed, as illustrated in FIG. 2, and a needle (not illustrated) may be optionally attached. A preferred example of each constituent will be explained below.

The syringe barrel 2 is constituted by a bottomed cylindrical member having a bottom 21, and a reduced diameter portion 22 of which the diameter is reduced than that of the trunk of the syringe barrel 2 is formed integrally in the central portion of the bottom 21. The reduced diameter portion 22, in which, for example, a hub for a needle pipe, various connectors, a tube, a catheter and/or the like for administrating a drug solution, collecting blood, and/or the like (not illustrated) are fitted and mounted, is used.

A reservoir space 24 for reserving a drug solution is formed in a portion surrounded by the syringe barrel 2 and the gasket 3. The reservoir space 24 communicates with the nozzle 23 in the reduced diameter portion 22. Therefore, a drug solution in the reservoir space 24 is discharged from the inside of the syringe barrel 2 to the outside through the nozzle 23 by pushing the gasket 3 toward the nozzle 23. Also, a desired drug solution may be previously reserved in the reservoir space 24.

Furthermore, it is preferable to form a plate-shaped flange 25 integrally on the proximate end of the syringe barrel 2. For carrying out the manipulation for moving the plunger 4 relatively to the syringe barrel 2, the finger can be placed on the flange 25 to carry out the manipulation.

The syringe barrel 2 is preferably constituted by a transparent (colorless transparent), colored transparent or semitransparent resin to secure the visibility of the reservoir space 24.

Examples of the constituent material of the syringe barrel 2 according to the present invention include, but are not particularly limited to, quartz glass; polyesters such as polyethylene terephthalate and copolymerized polyethylene terephthalate; acrylic resins such as polyacrylonitrile, polymethyl methacrylate and polymethacrylic acid; polyolefins such as polypropylene and polyethylene; polyvinyl chloride; polyamide such as nylon; polystyrene, polyethylene naphthalate, cyclic polyolefins (such as a copolymer of ethylene and tetracyclo[4.4.0.12.5.17.10]-3-dodecene), polypropylene, polystyrene, polymethylpentene, polycarbonate, polysulfone, and the like, and especially polypropylene and cyclic polyolefins are preferred.

Use of any material described above as the constituent material of the syringe barrel 2 is preferred from the viewpoint of peeling resistance in the case of surface modification with a polymer containing zwitterion according to the present invention.

In the syringe barrel 2, the gasket 3 is stored (disposed). The gasket 3 includes a fitting portion (hollow portion) 31, and a head portion 43 of the plunger 4 is fitted with the fitting portion 31.

The gasket 3 is constituted by a generally cylindrical member and has an outer surface on which two ring-shaped projections 32 which protrudes toward the inner surface 26 of the syringe barrel 2 are longitudinally formed at a specified spacing. More specifically, FIG. 1 illustrates two connected units of which each unit is a generally cylindrical member in which the bottom faces of tapered hollow cylinders symmetrical to an axis, are connected to each other. Although the two units are connected in FIG. 1, generally cylindrical members in which the bottom faces of tapered hollow cylinders symmetrical to a plurality of axes are connected to each other may also be connected to have a bellows shape. Further, the axial length of the gasket 3 having a structure as illustrated in FIG. 1 is decreased by inwardly deforming a recess 33 by an axial force. These projections 32 slide while brought into intimate contact with the inner surface 26 of the syringe barrel 2 to more surely maintain liquid-tightness and to allow improvement in slidability.

Figure 3:
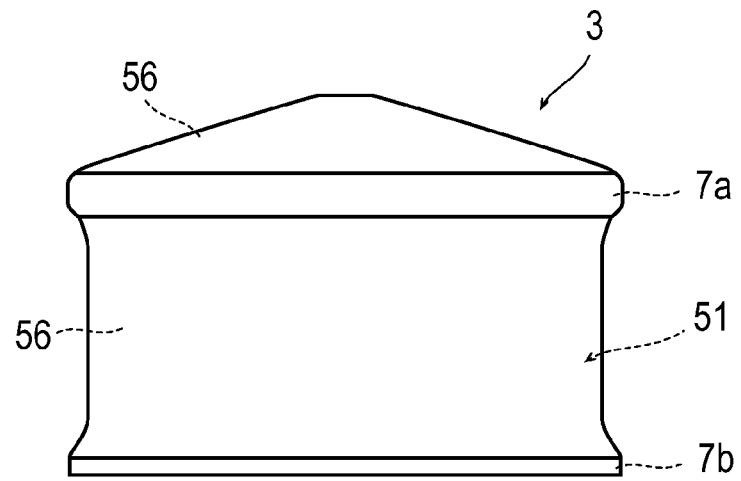
FIG. 3 is a front view of an example of a gasket according to the present invention.
Figure 4:
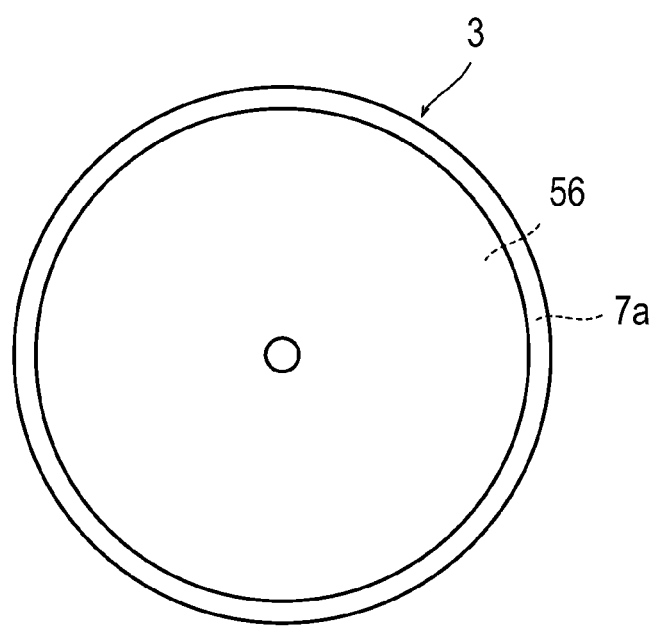
FIG. 4 is a plan view of the gasket according to the present invention in FIG. 3.
Figure 5:
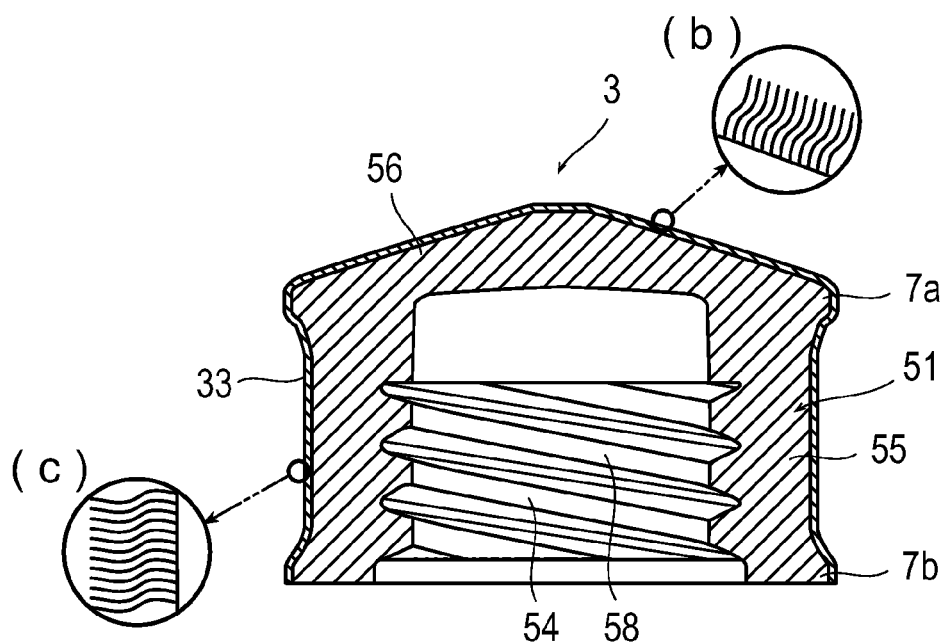
FIG. 5 is a cross-sectional view of the gasket according to the present invention in FIG. 3.
Figure 6:
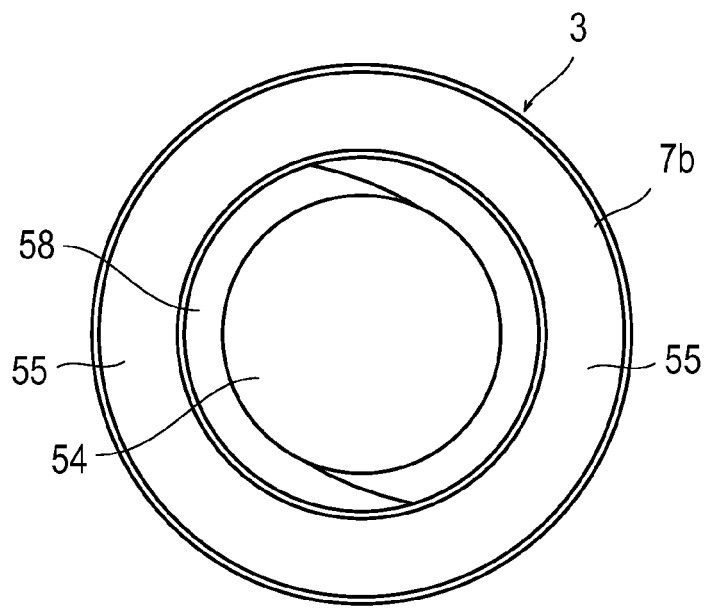
FIG. 6 is a bottom view of the gasket according to the present invention in FIG. 3.

Furthermore, in accordance with another embodiment of the gasket 3 according to the present invention, annular rims may be disposed on the top and rear sides of the gasket 3, as illustrated in FIGS. 3 to 6. FIG. 3 is the front view of the gasket 3; FIG. 4 is the plan view of the gasket 3 in FIG. 3; FIG. 5 is the cross-sectional view of the gasket 3 in FIG. 3; and FIG. 6 is the bottom view of the gasket 3 in FIG. 3. Specifically, a core portion 51 in the gasket 3 includes a gasket body portion 55 which extends in the approximately same outer diameter; a gasket taper portion 56 which is disposed in the top side of the gasket body portion 55 and has a diameter reduced in a tapered shape toward the top side; a plunger attaching portion 54 which is disposed on the inside from the proximate end of the gasket body portion 55 toward the top side; a top side annular rim 7a which is disposed on the side surface of the top of the gasket body portion 55; and a rear side annular rim 7b which is disposed on the side surface of the rear of the gasket body portion 55. Further, the top side annular rims 7a, 7b are compressed and deformed in the syringe barrel 2 since they are produced to have sizes slightly larger than the inner diameter of the syringe barrel 2. Although the two annular rims are disposed in the drawings, three or more may also be disposed.

Such a gasket 3 is coupled with the plunger 4 for manipulation for longitudinally moving the gasket 3 in the syringe barrel 2.

Examples of the constituent material of the gasket 3 according to the present invention include various rubber materials such as natural rubber, butyl rubber, isoprene rubber, butadiene rubber, styrene-butadiene rubber and silicone rubber; various thermoplastic elastomers based on polyurethane, polyester, polyamide, olefin, styrene and the like; and the like, and especially natural rubber, butyl rubber, and polyurethane-based thermoplastic elastomer are preferred.

Use of any of the above-described materials as the constituent material of the gasket 3 is preferred from the viewpoint of further improving slidability to allow smooth manipulation in the case of surface modification with a polymer containing zwitterion according to the present invention.

The plunger 4 according to the present invention is constituted mainly by a member having a cross-shaped cross section and has the top side on which a plate member 41 is formed integrally. Further, a plate-shaped (discal) flange 42 is formed integrally on the proximate end of the plunger 4. The plunger 4 is manipulated by placing the finger or the like on the flange 42.

Further, a mushroom-shaped head portion (coupler) 43 which is inserted into and fitted with the fitting portion 31 of the gasket 3 is formed in the top of the plunger 4. A method for fixation to the gasket 3 of the plunger 4 may also be a method such as swaging, fusion, adhesion with an adhesive, or threaded engagement, instead of fitting. The gasket 3 is connected to the plunger 4 by fitting in FIG. 1 and by screwing in FIG. 2. More particularly, in FIGS. 5 and 6, the plunger attaching portion 54 is a generally cylindrical recess which extends from the proximate end to the vicinity of the top in the gasket body portion 55, and a threaded engagement portion 58 which can be engaged threadedly with a screw type of engagement portion formed in the top of the plunger is disposed on the side surface of the recess. The top surface of the recess is approximately flatly formed.

Examples of the constituent material of the plunger 4 according to the present invention include polyvinyl chloride, polyethylene, polypropylene, polystyrene, poly-(4-methyl-pentene-1), polycarbonate, acrylic resins, acrylonitrile-butadiene-styrene copolymers, polyesters such as polyethylene terephthalate, butadiene-styrene copolymers, and polyamides (e.g., nylon 6, nylon 6-6, nylon 6-10, nylon 12), and polypropylene is most preferred.

Drug solutions which may be used in the syringe for prefilled syringe according to the present invention include various drug solutions like blood, glucide injections such as glucose, injection solutions for adjusting electrolytes, such as sodium chloride and potassium lactate etc., vitamins, vaccines, antibiotic injections, contrast media, steroids, protease inhibitors, fat emulsions, anticancer agents, anesthetic drugs, stimulants and narcotics, a wide variety of medical solutions with such narcotizing effect; and liquids such as distilled water, disinfectants, fluid diets and alcohols.

The inner wall of the syringe barrel according to the present invention is subjected to surface modification with a polymer containing zwitterion, and the inner wall of the syringe barrel and the surface of the gasket are preferably subjected to surface modification with the polymer. That is, the polymer containing zwitterion is directly or indirectly immobilized by chemical bond on the surface of the inner wall of the syringe barrel according to the present invention and/or the surface of the gasket. A surface subjected to surface modification with an oligoethyleneglycol chain is considered to be able to approximately completely prevent the adsorption of a protein (Ostuni, E., Chapman, R. G., Holmlin, R. E., Takayama, S., Whitesides, G. M.: A Survey of Structure-Property Relationship of Surfaces that Resist the Adsorption of Protein. Langmuir (2001), 17(18), 5605-5620)); and the reason of it is considered to be because the adsorption of a protein is inhibited by hydration by a hydrogen bond to an ether moiety in the oligoethyleneglycol chain in a solution and the contribution (excluded volume effect) of a three-dimensional repulsive force due to unsteady drifting of the oligoethyleneglycol chain in such a manner as that of kelp in a sea. Accordingly, in accordance with the present invention, surface modification with the polymer having zwitterion, which results in further expected ionic hydration as well as the two effects described above and has higher protein and agent non-adsorption abilities is carried out, thereby further inhibiting the adsorption of a low-molecular agent and a protein for a long term. Moreover, in accordance with the present invention, there can be provided the syringe for prefilled syringe, which has higher slidability and allows smoother manipulation than in the case of applying a silicone oil, by also subjecting a gasket portion to the surface modification with the polymer containing zwitterion. Furthermore, stricter control of the kind and surface density of the polymer containing zwitterion allows the provision of the syringe for prefilled syringe which further inhibits the adsorption of a low-molecular medical agent and a protein for a long term and has higher slidability.

The polymer containing zwitterion according to the present invention may be a polymer having betaine structure having anionic ion and cationic ion present together at non-adjacent position (it is called a polymer containing zwitterion because it has both anionic ion and cationic ion). In the betaine structure, it is preferable that anionic ion moiety and cationic ion moiety are chemically bonded via a linker group. The anionic ion moiety includes, for example, carboxylate ion (—COO⁻), sulfate ion (-OSO₃⁻), sulfonate ion (—SO₃⁻), and the cationic ion moiety includes, for example, quaternary ammonium ion (—N($R_x$)($R_y$)₂⁺: $R_x$ represents an alkylene group having 1 to 6 carbon atoms, $R_y$ independently represents a substituent group except for hydrogen atom, preferably an alkyl group having 1 to 6 carbon atoms, substituted alkyl group, aryl group, substituted aryl group). In addition, the linker group is preferably an alkylene group having 1 to 6 carbon atoms.

In addition, the polymer containing zwitterion according to the present invention is preferably at least one selected from the group comprising of the following chemical formulae (1) to (4) (chemical formula (1), chemical formula (2), chemical formula (3) and chemical formula (4)):

chemical formula (1)

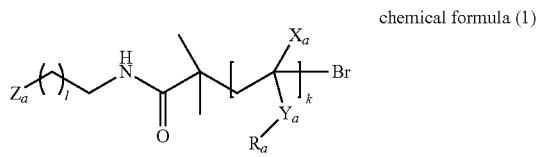

wherein $X_a$, $Y_a$ and $Z_a$ are each independent;
$X_a$ is preferably hydrogen atom or methyl group;
$Y_a$ is preferably —C(O)O— or —C(O)NH—;
$Z_a$ is preferably —OH group, —SH group or —Si(OR)₃, wherein R is preferably at least one group selected from the group consisting of hydrogen atom, methyl group, and ethyl group;
$X_a$ is more preferably methyl group;
$Y_a$ is more preferably —C(O)O—;
$Z_a$ is more preferably —SH group, wherein $R_a$ is preferably betain group, and the betain group is preferably the group below-described formula (1):

*-A₁-L-A₂    formula (1)

wherein A₁ and A₂ are each independent;
A₁ is preferably a quaternary ammonium ion ((—($R_x$)—N($R_y$)₂($R_z$)—)⁺);
$R_x$ represents an alkylene group having 1 to 6 carbon atoms, $R_y$ independently represents an alkyl group having 1 to 6 carbon atoms, and $R_z$ represents a single bond binding to linker group;
A₂ is preferably at least one selected from the group consisting of carboxylate ion (—COO⁻), phosphate ion (—OPO₃²⁻), sulfate ion (-OSO₃⁻), and sulfonate ion (—SO₃⁻);
L preferably represents an alkylene group having 1 to 6 carbon atoms,
k and l which are a polymerization degree are each independent;
k is preferably an integer of 1 to 100,000, more preferably an integer of 1,000 to 35,000;
l is preferably an integer of 1 to 18, more preferably an integer of 6 to 12; and
$R_a$ is more preferably sulfobetaine group or carboxybetaine group, and particularly preferably the following chemical formula (A):

chemical formula (A)

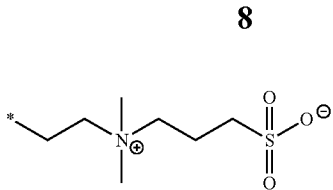

or the following chemical formula (B):

chemical formula (B)

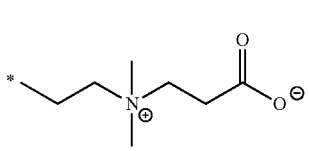

chemcial formula (2)

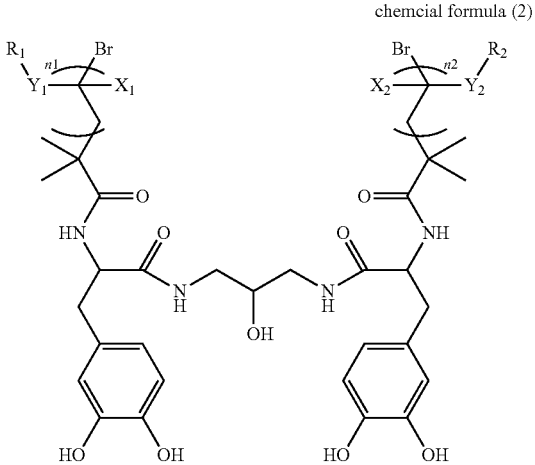

wherein X₁, X₂, Y₁ and Y₂ are each independent;
X₁ and X₂ are hydrogen atom or methyl group;
Y₁ and Y₂ are —C(O)O— or —C(O)NH—;
n1 and n2 which are a polymerization degree are each independent;
n1 is preferably an integer of 1 to 100,000, more preferably an integer of 1,000 to 35,000;
n2 is preferably an integer of 1 to 100,000, more preferably 1,000 to 35,000; and
R₁ and R₂ are preferably betain group, and the betain group is more preferably defined by the above-described formula (1), is further preferably sulfobetaine group or carboxybetaine group, and particularly preferably the following chemical formula (A):

chemical formula (A)

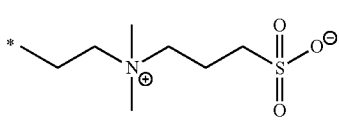

or the following chemical formula (B):

chemical formula (B)

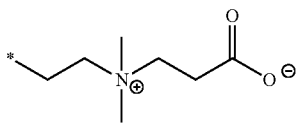

chemical formula (3)

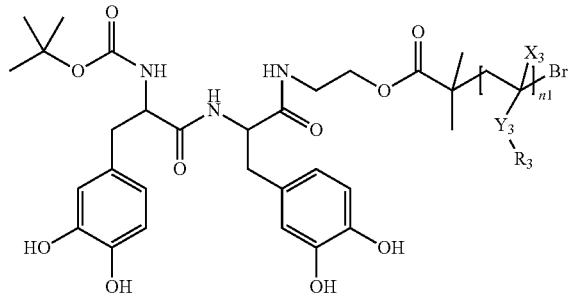

wherein $X_3$ and $Y_3$ are each independent;
$X_3$ is hydrogen atom or methyl group;
$Y_3$ is —C(O)O— or —C(O)NH—;
n1 which is a polymerization degree is preferably an integer of 1 to 100,000, more preferably an integer of 1,000 to 35,000; and $R_3$ described above is preferably betain group, and the betain group is more preferably defined by the above-described formula (1), is further preferably sulfobetaine group or carboxybetaine group, and particularly preferably the following chemical formula (A):

chemical formula (A)

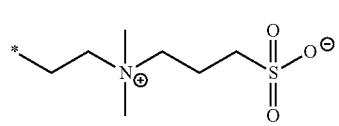

or the following chemical formula (B):

chemical formula (B)

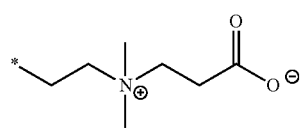

chemical formula (4)

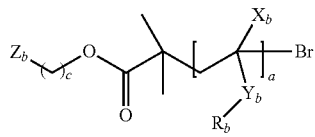

wherein $X_b$, $Y_b$ and $Z_b$ are each independent;
$X_b$ is preferably hydrogen atom or methyl group;
$Y_b$ is preferably —C(O)O— or —C(O)NH—;
$Z_b$ is preferably —OH group, —SH group or —Si(OR)$_3$, wherein R is preferably at least one group selected from the group consisting of hydrogen atom, methyl group, and ethyl group;
$X_b$ is preferably methyl group;
$Y_b$ is preferably —C(O)O—;
$Z_b$ is preferably —SH group, wherein $R_b$ is preferably betaine group, and the betain group is more preferably defined by the above-described formula (1), is further preferably sulfobetaine group or carboxybetaine group;
a and c which are a polymerization degree are each independent and are preferably an integer of 1 to 100,000, more preferably an integer of 1,000 to 35,000; and $R_b$ is particularly preferably the following chemical formula (A):

chemical formula (A)

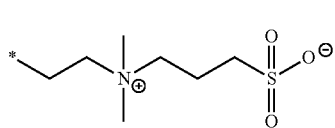

or the following chemical formula (B).

chemical formula (B)

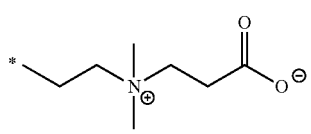

The alkylene group having 1 to 6 carbon atoms of the present invention includes methylene, ethylene, propylene, isopropylene, butylene, isobutylene, sec-butylene, tert-butylene, pentylene, iso-pentylene, hexylene, etc. The alkyl group having 1 to 6 carbon atoms in the present invention includes methyl group, ethyl group, n-propyl group, isopropyl group, cyclopropyl group, n-butyl group, isobutyl group, sec-butyl group, tert-butyl group, cyclobutyl group, n-pentyl group, isopentyl group, neopentyl group, 1,2-dimethylpropyl group, cyclopentyl group, n-hexyl group, cyclohexyl group, 1,3-dimethylbutyl group, 1-isopropyl propyl group, etc.

The polymer containing zwitterion according to the present invention is more preferably the polymer containing zwitterion represented by the chemical formula (1) or the chemical formula (4), further preferably carboxybetaine in which a carboxyl group is bound to its terminal. The reason why carboxybetaine is particularly preferred is because further good protein and agent non-adsorption properties can be achieved by the inhibition of breaking of the clustering structure of water and the occurrence of milder hydration in comparison with other betaines.

"The inner wall surface of the syringe barrel (and/or the gasket surface) is subjected to surface modification with the polymer containing zwitterion" in accordance with the present invention means that any polymer described in the above-described chemical formulae (1) to (4) is chemically bonded or immobilized directly to the inner wall surface of the syringe barrel (and/or the gasket surface) or directly to a primer layer described below and any polymer residue described in the above-described chemical formulae (1) to (4) is substantially present on the inner wall surface of the syringe barrel (and/or the gasket surface). Further, the surface of the gasket refers to a pressurization surface located in the top of the gasket in the surface of the gasket and a gasket side surface contacting with the inner wall of the syringe barrel in the surface of the gasket.

Therefore, all the four OH groups are preferably chemically bonded directly to the inner wall surface of the syringe barrel or directly to the primer layer described below at a site, in which $Z_a$ at the polymer terminal is chemically bonded directly to the surface of the gasket and the inner wall surface of the syringe barrel or directly to the primer layer described below, in the above-described chemical formula (1), at a site, in which any one of the OH groups bound to the benzene ring having a catechol structure is chemically bonded, in the above-described chemical formulae (2) and (3), and at a site in which the $Z_b$ group at the polymer terminal is chemically bonded in the above-described chemical formula (4).

It is considered that, as a result, not only the adsorption of an agent and a protein can be suppressed and prevented by three-dimensional repulsion since a polymer chain which is movable in a solution can be immobilized on the surface of the gasket and/or the inner wall surface of the syringe barrel, but also, since a zwitterion in the polymer according to the present invention can be localized on a surface contacting with a drug solution, the zwitterion can act as a functional group with an acceptor property for a proton (intermolecular hydrogen bond) to allow the effective suppression and prevention of the protein adsorption.

The molecular weight (number average molecular weight) of the polymer containing zwitterion according to the present invention is preferably 200 to 2,000,000, more preferably 20,000 to 1,000,000, particularly preferably 200,000 to 800,000.

The molecular weight of the polymer containing zwitterion, ranging from 20,000 to 80,000, is preferred from the viewpoint of the adsorption of a low-molecular agent and a protein.

Further, the molecular weight of the polymer containing zwitterion, ranging from 200,000 to 800,000, is preferred from the viewpoint of high slidability and smooth manipulatability.

Methods for measuring a number average molecular weight include GPC, a light scattering method, viscosimetry and mass spectrometry (TOFMASS, etc.), and the number average molecular weight of the polymer containing zwitterion according to the present invention is measured by GPC (device name: Waters 2695 Separation Module).

When the polymer containing zwitterion according to the present invention is immobilized on the surface of the gasket and the inner wall surface of the syringe barrel, the polymer may be directly or indirectly immobilized on the surface of the gasket and/or the inner wall surface of the syringe barrel, and a primer layer may be formed on the surface of the gasket and/or the inner wall surface of the syringe barrel when it is indirectly immobilized.

The primer layer according to the present invention is appropriately selected depending on the material of the gasket used and the material of the syringe barrel, in which a coupling agent, a polylysine solution, a Ti thin film, a silicon thin film and a Au thin film are preferably coated on the surface of the gasket and/or the inner wall surface of the syringe barrel.

As a method for forming the Ti thin film, the $TiO_2$ thin film, the silicon thin film, the oxidized silicon thin film and the Au thin film on the surface of the gasket and/or the inner wall surface of the syringe barrel, any method may be used, in which a physical vapor growth method such as a vacuum deposition method, a sputtering method, an ion plating method or a molecular beam epitaxy (MBE) method; a chemical vapor deposition (CVD) method such as plasma polymerization; an electroplating method; an electroless plating method; or the like may be used. Further, the method is performed by forming a film by a solution process when a coupling agent is used. That is, it refers to a method of dissolving the coupling agent in a solvent in which the coupling agent can be dissolved and forming a film using the solution. Specifically, a common method such as a cast method, a blade coating method, a wire bar coating method, a spray coating method, a dipping (dip) coating method, a bead coating method, an air knife coating method, a curtain coating method, an inkjet method, a spin coating method or a Langmuir-Blodgett (LB) method may be used.

Also, known pretreatment may be optionally performed before forming a primer layer. Particularly, when a synthetic resin is employed as the material of the gasket and the material of the syringe barrel, their surfaces may also be subjected to plasma treatment and DUV (Deep UV, far infrared) irradiation treatment.

The thickness of the primer layer is preferably 0.001 to 1 μm, more preferably 0.002 to 0.2 μm.

The thickness of the primer layer, ranging from 0.002 to 0.2 μm, is preferred from the viewpoint of peel resistance.

A contact angle between the inner wall of the syringe barrel subjected to surface modification with the polymer containing zwitterion according to the present invention and water is, for example, preferably 0 to 90°, more preferably 0 to 30°.

The contact angle ranging from 0 to 30° results in a hydrophilic surface and is preferred from the viewpoint of suppressing and preventing the adsorption of a protein.

A contact angle between a pressurization surface located in the top of the gasket subjected to surface modification with the polymer containing zwitterion according to the present invention and water is, for example, preferably 0 to 90°, more preferably 0 to 30°.

The contact angle ranging from 0 to 30° results in a hydrophilic surface and is preferred from the viewpoint of suppressing and preventing the adsorption of a protein.

A contact angle between a gasket side surface contacting with the inner wall of the syringe barrel subjected to surface modification with the polymer containing zwitterion according to the present invention and water is, for example, preferably 0 to 90°, more preferably 0 to 30°.

The contact angle ranging from 0 to 30° results in a hydrophilic surface and is preferred from the viewpoint of suppressing and preventing the adsorption of a protein.

Known methods and apparatuses can be used for the measurement of a contact angle in accordance with the present invention, and it is measured using a contact angle meter (DM301) manufactured by Kyowa Interface Science Co., Ltd. in accordance with the present invention.

The amount (density) of surface modification with the polymer containing zwitterion according to the present invention per unit area is appropriately selected depending on a part to be subjected to the modification; and, in the case of the surface modification on the inner wall of the syringe barrel, the density of the polymer containing zwitterion per unit area is preferably 0.5 μg to 5 mg/cm$^2$, more preferably 1 μg to 100 μg/cm$^2$.

In the case of the syringe for prefilled syringe, the inner wall of the syringe barrel is suppressed and prevented from adsorbing a medical agent, a protein or the like in a drug solution and also has an influence on the slidability of the gasket because of directly contacting with the gasket, and therefore the density of the polymer is preferably 2 μg to 50 μg/cm$^2$.

Further, in the case of the surface modification on a pressurization surface located in the top of the gasket in the gasket surface, the density of the polymer containing zwitterion per unit area is preferably 0.5 μg to 5 mg/cm$^2$, more preferably 1 μg to 100 μg/cm$^2$.

Since the pressurization surface located in the top of the gasket in the gasket surface does not contact with the inner wall of the syringe barrel, the adsorption of an agent, a protein or the like in a drug solution is generally suppressed and prevented, and therefore the density of the polymer is preferably 2 μg to 50 μg/cm$^2$.

Furthermore, in the case of the surface modification on the gasket side surface contacting with the inner wall of the syringe barrel in the gasket surface, the density of the polymer containing zwitterion per unit area is preferably 0.5 μg to 100 mg/cm², more preferably 10 μg to 50 mg/cm².

Since the gasket side surface does not contact generally with the drug solution and is a part that generally contacting directly with the inner wall of the syringe barrel, it has an influence on the slidability of the gasket on the syringe barrel, and therefore the density of the polymer is preferably 50 μg to 25 mg/cm².

The polymer containing zwitterion according to the present invention preferably has a length in the order of "the chain length (a) of the polymer containing zwitterion, with which surface modification is performed on the inner wall of the syringe barrel"≤"the chain length (b) of the polymer containing zwitterion, with which surface modification is performed on a pressurization surface located in the top of the gasket in the gasket surface"≤"the chain length (c) of the polymer containing zwitterion, with which surface modification is performed on a gasket side surface contacting with the inner wall of the syringe barrel in the gasket surface".

In accordance with the polymer containing zwitterion according to the present invention, the chain lengths (a), (b) and (c) are indicated by the following expression:

$$(a) \leq (b) \leq (c) \qquad \text{formula (1)}$$

in which, particularly, the case of meeting (a)=(b)≤(c) is most preferred from the viewpoint of compatibility between the non-adsorption of a protein and an agent and improvement in slidability.

Preferred embodiments of the syringe for prefilled syringe according to the present invention will be explained below together with a surface modification method. A syringe barrel, a plunger and a gasket, each produced by a known method, are prepared.

FIG. 1, FIG. 2 and FIG. 5 illustrate the relationship of the chain length (a) of a polymer containing zwitterion, with which surface modification is performed on the inner wall of the syringe barrel, the chain length (b) of a polymer containing zwitterion, with which surface modification is performed on a pressurization surface located in the top of the gasket in a gasket surface, and the chain length (c) of a polymer containing zwitterion, with which surface modification is performed on a gasket side surface contacting with the inner wall of the syringe barrel in the gasket surface.

(First Preferred Method for Surface Modification of Syringe Barrel)

When the syringe barrel is made of glass, it is dipped overnight in an NaOH solution, washed with distilled water, thereafter subjected to UV irradiation, washed with ethanol and distilled water, and dried with a nitrogen gas, followed by applying a known silane coupling agent (e.g., an ethanol solution containing the following chemical formula (5)) to the inner wall of the syringe barrel. Then, the syringe barrel to which the silane coupling agent is applied is heated to predetermined temperature (100° C.) under reduced pressure. Furthermore, a solution in which CuBr, 2,2'-dipyridine and SBMA of the following chemical formula (6) or CBMA of the following chemical formula (7) are added to a water and methanol solvent is applied to the inner wall of the syringe barrel to effect atom transfer radical polymerization.

Chemical formula (5)
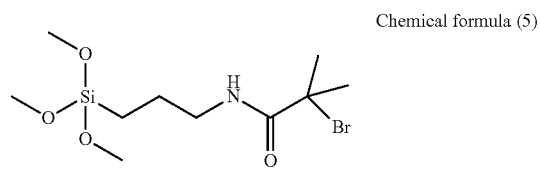

Chemical formula (6)
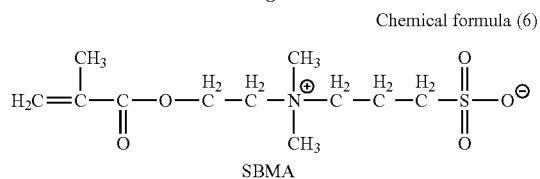
SBMA

Chemical formula (7)
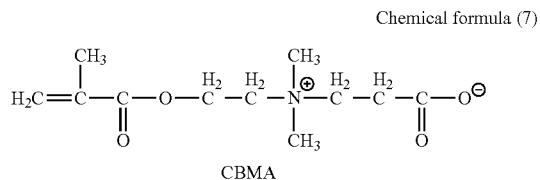
CBMA

When the syringe barrel is made of a synthetic resin, the same process as described above is carried out except that its surface is subjected to plasma treatment prior to applying a silane coupling agent (e.g., ethanol solution containing the chemical formula (5) described above).

Figure 7:
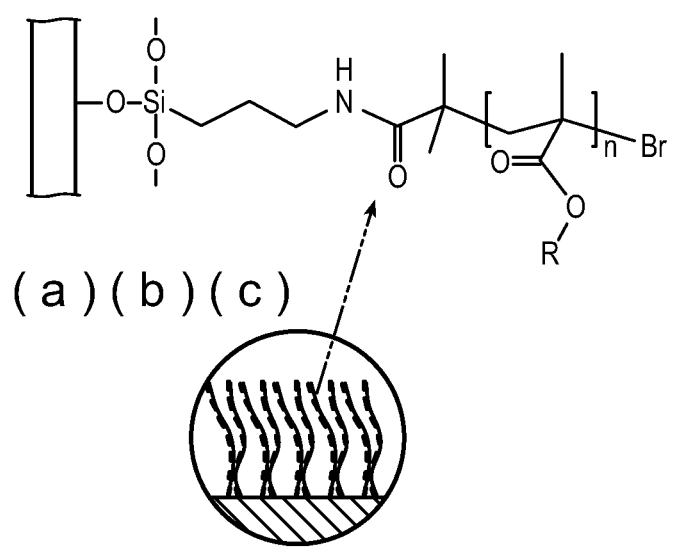
FIG. 7 is a schematic view that illustrates one aspect in which surface modification with a polymer containing zwitterion according to the present invention is performed.

The syringe barrel subjected to surface modification with the polymer containing zwitterion (chemical formula (1)) as illustrated in FIG. 7 can be produced by such an operation. As a reference indicating such a production method in detail, see Zheng Zhang, et al., Surperlow Fouling Sulfobetaine and Carboxybetaine Polymers on Glass Slides. Langmuir (2006), 22, 10072-10077.

(Second Preferred Method for Surface Modification of Syringe Barrel)

A syringe barrel subjected to surface modification (immobilization) by coating polymers containing zwitterion (chemical formulae (2, 3)) at the DOPA terminal illustrated in FIG. 8 can be produced by preparing solutions in which the polymers containing zwitterion of the chemical formulae (2) and/or (3) obtained in the following reaction formulae (1) and (2) are added to a solvent (water and THF), thereafter applying the solutions to the inner wall of the syringe barrel of which the inner wall is coated with a titanium oxide thin film (20 μm) by a CVD method, and drying the solutions (see FIG. 8).

Reaction formula (1)
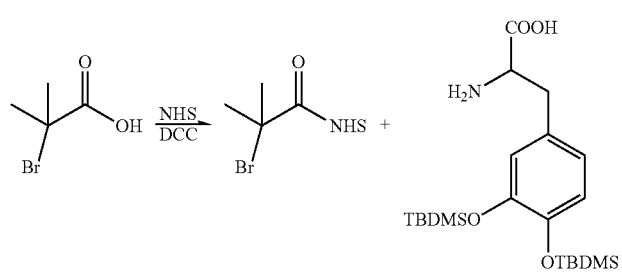
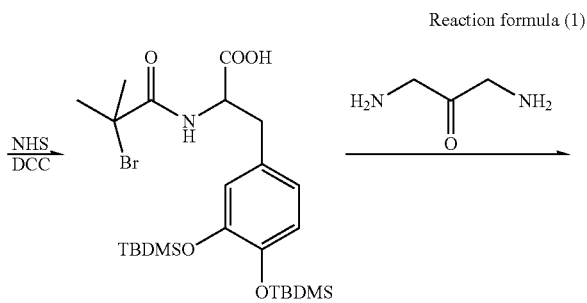

-continued
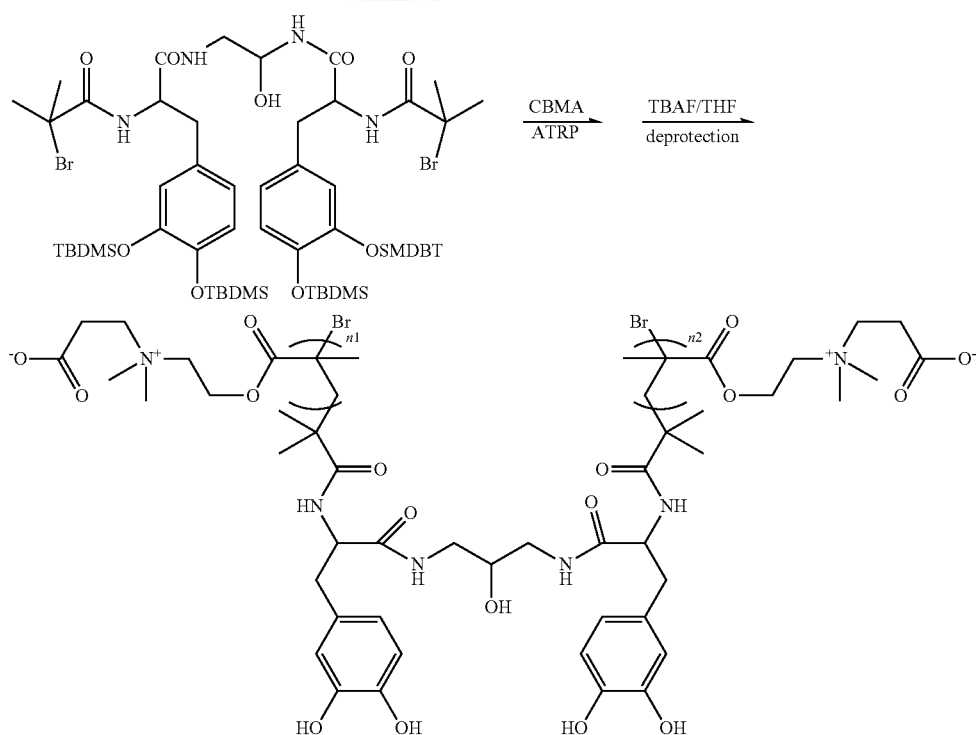
Polymer of chemical formula (2)
Reaction formula (2)
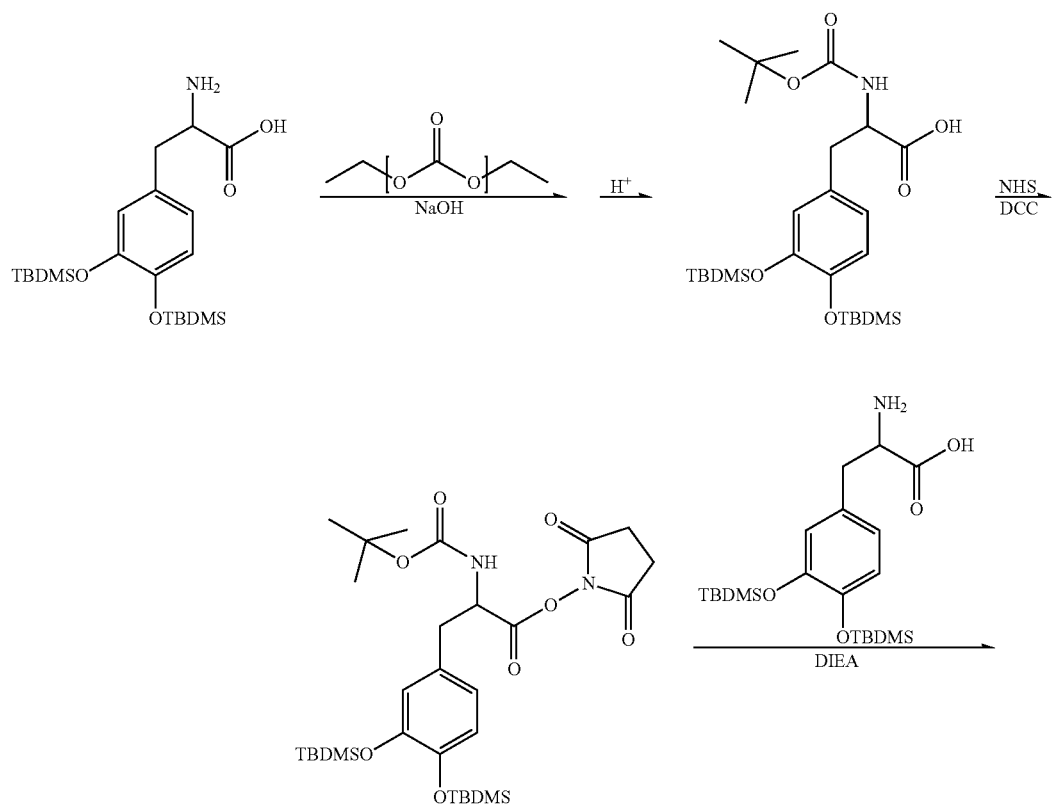

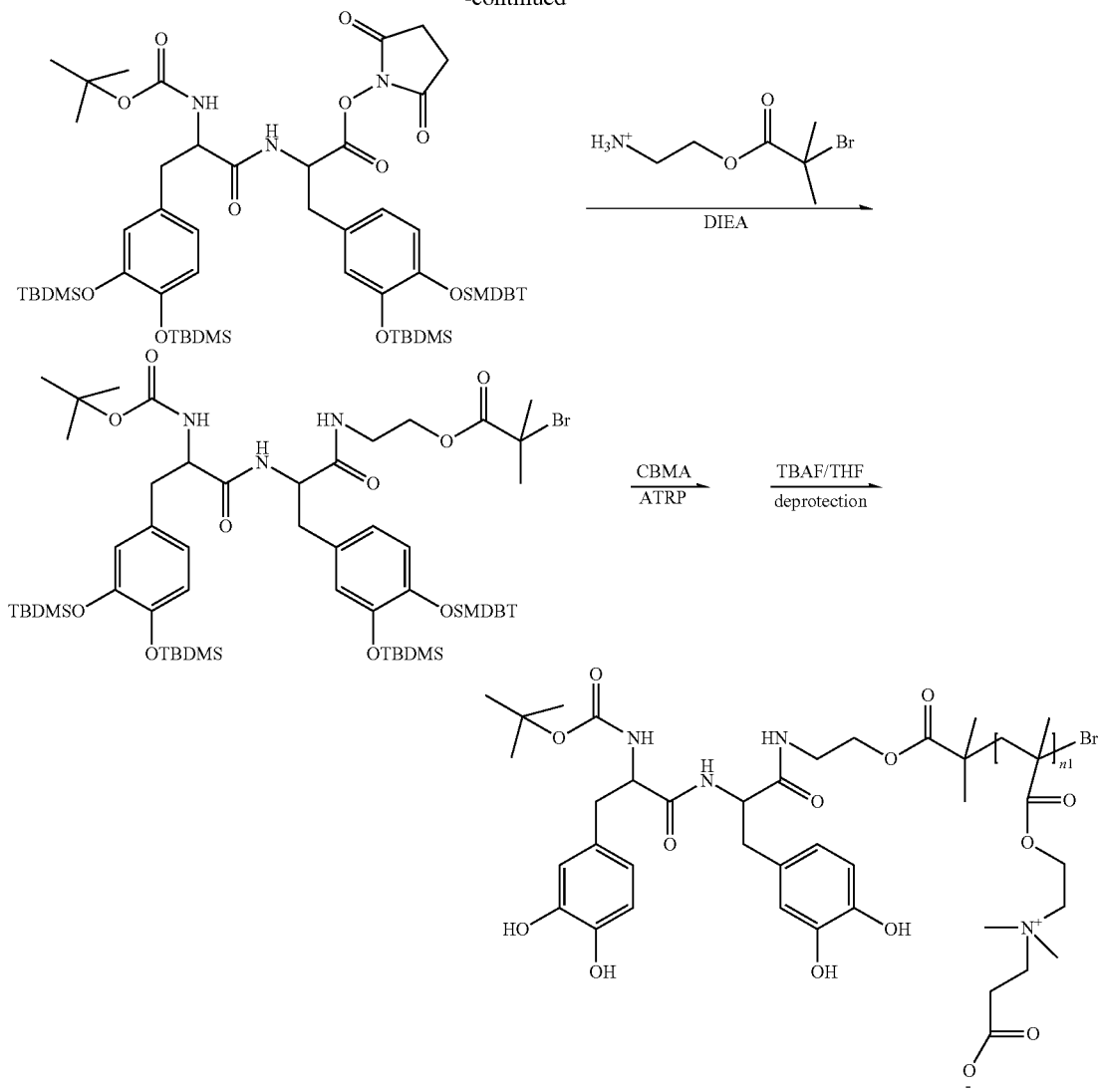

Polymer of chemical formula (3)

In the reaction formulae (1) and (2) described above, NHS, TBDMS, DCC, TBAF and DIEA are abbreviations of N-hydroxysuccinimide, t-butyl chlorodimethylsilane, dicyclohexylcarbodiimide, tetrabutylammonium fluoride and N,N-diisopropylethylamine, respectively.

As a reference indicating such a production method in detail, see Langmuir 2005, 21, 640-646, $TiO_2$ (20 nm) by physical vapor deposition using reactive magnetron sputtering (PSI, Villigen, Switzerland).

(First Preferred Method for Surface Modification of Gasket)

A gasket is dipped overnight in an NaOH solution, washed with distilled water, thereafter subjected to UV irradiation, washed with ethanol and distilled water, and dried with a nitrogen gas to subject a gasket surface to plasma treatment, followed by applying a known silane coupling agent (e.g., an ethanol solution containing the chemical formula (5) described above) to the gasket surface. Then, the gasket to which the silane coupling agent is applied is heated to predetermined temperature (100° C.) under reduced pressure. Furthermore, a solution in which CuBr, 2,2'-dipyridine and SBMA of the chemical formula (6) described above or CBMA of the chemical formula (7) described above are added to a water and methanol solvent is applied to the surface of the gasket to effect atom transfer radical polymerization.

The gasket subjected to surface modification with the polymer containing zwitterion (chemical formula (1)) as illustrated in FIG. 7 can be produced by such an operation. A reference indicating such a production method in detail is the same as described above.

(Second Preferred Method for Surface Modification of Gasket)

Figure 8:
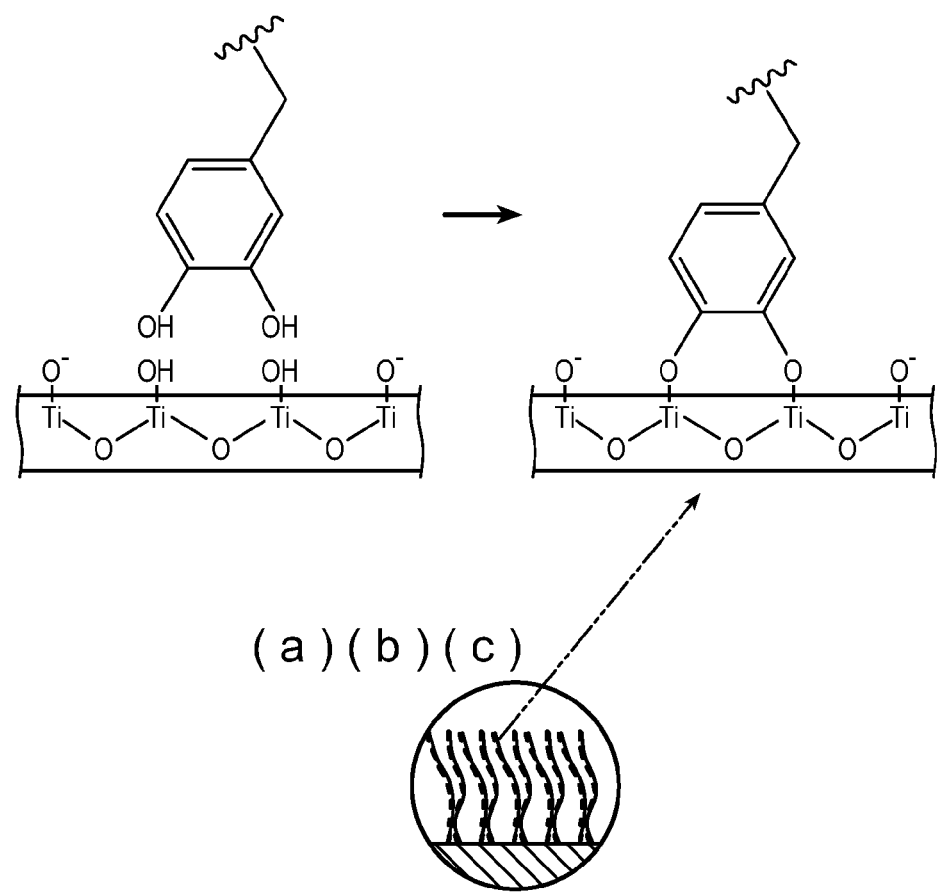
FIG. 8 is a schematic view that illustrates one aspect in which surface modification with a polymer containing zwitterion according to the present invention is performed.

A gasket subjected to surface modification with polymers containing zwitterion (chemical formulae (2, 3)) illustrated in FIG. 8 can be produced by preparing solutions in which the polymers containing zwitterion of the chemical formulae (2) and/or (3) obtained in the reaction formulae (1) and (2) described above are added to a solvent (water and THF), thereafter applying the solutions to the surface of the gasket of which the surface is coated with a titanium oxide thin film by a CVD method, and drying the solutions. A reference indicating such a production method in detail is the same as described above.

(Third Preferred Method for Surface Modification of Gasket)

A solution in which ω-mercaptoundecyl-bromoisobutyrate of the following chemical formula (8) is added to a solvent (ethanol) is prepared, thereafter applied to the surface of a gasket of which the surface is coated with a gold thin film by a CVD method, and dried, followed by applying a solution, in which CuBr, 2,2'-dipyridine and SBMA of the chemical formula (6) described above or CBMA of the chemical formula (7) described above are added to a water and methanol solvent, to the surface of the gasket, to effect atom transfer radical polymerization.

Chemical formula (8):

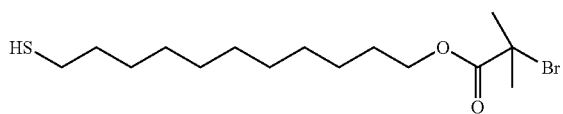

Figure 9:
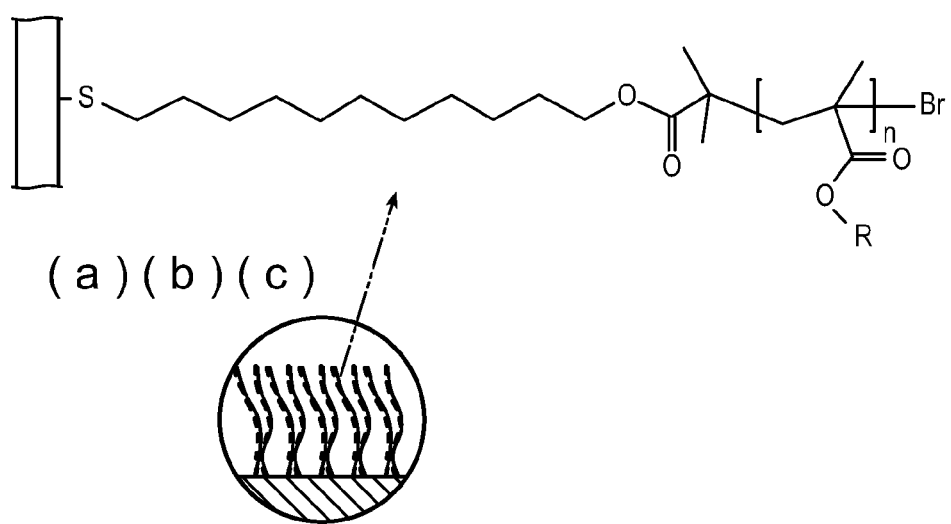
FIG. 9 is a schematic view that illustrates one aspect in which surface modification with a polymer containing zwitterion according to the present invention is performed.

The gasket subjected to surface modification with the polymer containing zwitterion (chemical formula (4)) as illustrated in FIG. 9 can be produced by such an operation. As a reference indicating such a production method in detail, see Zheng Zhang, et al., Blood compatibility of surfaces with superlow protein adsorption. Biomaterials 29 (2008), 4285-4291.

Further, all the three references described above are encompassed within the scope of the present invention.

In accordance with the syringe for prefilled syringe according to the present invention, the chain lengths (a), (b) and (c) preferably meet the following expression:

$$(a) \leq (b) \leq (c)$$

in which, particularly, the case of meeting (a)=(b)≤(c) is most preferred from the viewpoint of compatibility between the non-adsorption of a protein and an agent and improvement in slidability. In such a manner, in accordance with the syringe for prefilled syringe according to the present invention, the inner wall surface of (a) of the syringe barrel and the gaskets (b) and (c) are separately subjected to the treatment as a method for subjecting the inner wall surface of the syringe barrel, the pressurization surface of the gasket, and the side surface of the gasket to surface modification with the polymers containing zwitterion having the different chain lengths. Specifically, since chain lengths on the inner wall surface (a) of the syringe barrel may be uniform, the inner wall surface of the syringe barrel is optionally washed with an acid or subjected to pretreatment such as plasma treatment, followed by appropriately forming a metallic thin film with a polymer containing zwitterion, with which desired surface treatment is performed, by the above-mentioned method, to perform the surface treatment with the polymer containing zwitterion. Since chain lengths on (b) and (c) may also be uniform when the chain lengths on the side surface (b) of the gasket and the surface (c) of the taper portion of the gasket are equal, pretreatment is similarly optionally performed, followed by appropriately forming a metallic thin film with a polymer containing zwitterion, with which desired surface treatment is performed, by the above-mentioned method, to perform the surface treatment with the polymer containing zwitterion.

In a method for making the chain lengths different on the side surface (b) of the gasket and the taper portion surface (c) of the gasket, when, for example, polymers containing zwitterion are directly immobilized on the surface as in the case of the chemical formulae (2) and (3), the above-described pretreatment is optionally performed, thereafter the polymers having different chain lengths are previously prepared, first, any one of the side surface of the gasket or the taper portion surface of the gasket is masked with a resist resin, the polymer containing zwitterion is immobilized on the other, and the mask is thereafter removed to immobilize the polymers having the different chain lengths. The chain lengths can also be made to be different on the side surface (b) of the gasket and the taper portion surface (c) of the gasket by similarly masking one of the surfaces to sequentially perform graft polymerization when the graft polymerization of CBMA or SBMA from the surfaces is performed.

(Method for Evaluating Protein Adsorption)

For the gasket and the syringe barrel which are subjected to the surface modification with the polymer containing zwitterion obtained by the above-described method, a method for evaluating protein adsorption is briefly described below. Whether or not protein adsorption occurs on the gasket and syringe barrel surfaces subjected to surface modification with the polymer containing zwitterion is determined by a known measurement method, of which examples include infrared spectroscopy, ESCA, contact angle measurement, surface plasmon resonance angle measurement, and the like. It is preferable to measure the protein adsorption by the surface plasmon resonance angle measurement from the viewpoint of allowing the observation of the surfaces in a solution in situ.

For example, the inside of the syringe barrel and the gasket surface, subjected to surface modification with the polymer containing zwitterion according to the present invention, are washed with a phosphate buffer solution, distilled water and the like, and dried, and a part of the surface of the syringe barrel and a part of the surface of the gasket are cut into predetermined sizes to be tip-like pieces. Then, the pieces are set in a surface plasmon resonance angle device, and a flow cell is filled with a phosphate buffer solution (physiological conditions, etc.), followed by making a solution (0.1 to 100 mg/mL) containing a known protein such as fibrinogen or lysozyme flow as an analyte to observe a variation in resonance angle.

What is claimed is:

1. A syringe for prefilled syringe comprising:
a plunger in which a gasket is attached to a top; and
a syringe barrel in which the plunger is slidably stored,
wherein the syringe barrel includes an inner wall subjected to surface modification with a polymer containing zwitterion,
wherein the polymer containing zwitterion is at least one selected from the group consisting of the following chemical formula (2) and chemical formula (3):

chemical formula (2)

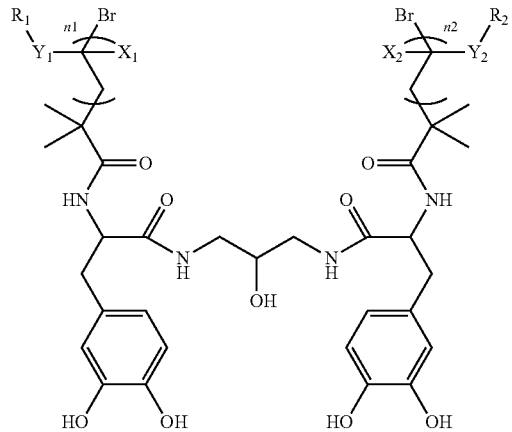

wherein $X_1$, $X_2$, $Y_1$ and $Y_2$ are each independent;
$X_1$ and $X_2$ are hydrogen atom or methyl group;
$Y_1$ and $Y_2$ are —C(O)O— or —C(O)NH—;

n1 and n2 which are a polymerization degree are each independent;
n1 is an integer of 1 to 100,000;
n2 is an integer of 1 to 100,000; and
$R_1$ and $R_2$ each independently represent a betaine group shown in the following formula (1):

*-$A_1$-L-$A_2$   formula (1)

wherein $A_1$ and $A_2$ are each independent;
$A_1$ is a quaternary ammonium ion $((-(R_x)-N(R_y)_2(R_z)-)^+)$, and wherein $R_x$ represents an alkylene group having 1 to 6 carbon atoms, $R_y$ independently represents an alkyl group having 1 to 6 carbon atoms, and $R_z$ represents a single bond binding to linker group;
$A_2$ is at least one selected from the group consisting of carboxylate ion ($-COO^-$), phosphate ion ($-OPO_3^{2-}$), sulfate ion ($-OSO_3^-$), and sulfonate ion ($-SO_3^-$);
L represents an alkylene group having 1 to 6 carbon atoms;

chemical formula (3)

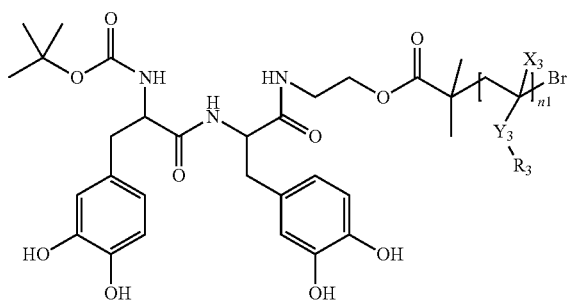

wherein $X_3$ and $Y_3$ are each independent;
$X_3$ is hydrogen atom or methyl group;
$Y_3$ is —C(O)O— or —C(O)NH—;
n1 which is a polymerization degree is an integer of 1 to 100,000; and
$R_3$ represents betaine group shown in the above-described formula (1).

2. The syringe for prefilled syringe according to claim 1, wherein the gasket comprises a surface subjected to surface modification with a polymer containing zwitterion.

3. The syringe for prefilled syringe according to claim 2, wherein the following expression:

$(a) \leq (b) \leq (c)$ is met assuming that the chain length of a polymer containing zwitterion, with which surface modification is performed on the inner wall of the syringe barrel is a chain length (a); the chain length of a polymer containing zwitterion, with which surface modification is performed on a pressurization surface located in a top of the gasket in the gasket surface is a chain length (b); and the chain length of a polymer containing zwitterion, with which surface modification is performed on a gasket side surface contacting with the inner wall of the syringe barrel in the gasket surface is a chain length (c).

4. The syringe for prefilled syringe of claim 1, wherein the formula (1) is either the following chemical formulae (A):

chemical formula (A)

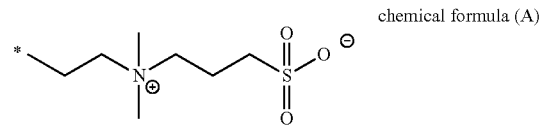

or the following chemical formula (B):

chemical formula (B)

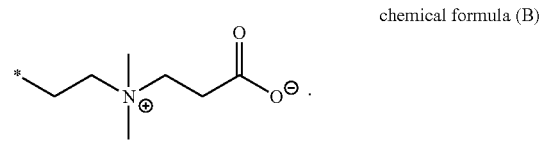 [SMILES: *CC[N+](C)(C)CCC(=O)[O-]]

5. The syringe for prefilled syringe according to claim 1, wherein the number average molecular weight of the polymer containing zwitterion is 200,000 to 800,000.

* * * * *